US008281646B2

(12) United States Patent
Waid et al.

(10) Patent No.: US 8,281,646 B2
(45) Date of Patent: Oct. 9, 2012

(54) MEASUREMENT TOOL AND METHOD OF USE

(75) Inventors: Margaret Cowsar Waid, Aledo, TX (US); Bryan W. Kasperski, Azle, TX (US); Michael Andrew Yuratich, Hamble (GB)

(73) Assignee: Precision Energy Services, Inc., Fort Worth, TX (US)

( * ) Notice: Subject to any disclaimer, the term of this patent is extended or adjusted under 35 U.S.C. 154(b) by 627 days.

(21) Appl. No.: 12/335,981

(22) Filed: Dec. 16, 2008

(65) Prior Publication Data

US 2009/0193889 A1 Aug. 6, 2009

(30) Foreign Application Priority Data

Dec. 22, 2007 (GB) .................................. 0725199.4

(51) Int. Cl.
*G01N 11/16* (2006.01)
(52) U.S. Cl. ........................ 73/54.41; 73/32 A; 73/54.02
(58) Field of Classification Search .................. 73/32 A, 73/54.41
See application file for complete search history.

(56) References Cited

U.S. PATENT DOCUMENTS

| 4,154,093 | A | * | 5/1979 | Smith et al. .................. 73/54.27 |
| 4,524,610 | A | | 6/1985 | Fitzgerald et al. |
| 5,253,533 | A | | 10/1993 | Lam et al. |
| 5,602,334 | A | | 2/1997 | Proett et al. |
| 7,805,988 | B2 | | 10/2010 | Kasperski et al. |
| 2001/0039829 | A1 | | 11/2001 | Wenger et al. |
| 2003/0233878 | A1 | | 12/2003 | Drahm et al. |
| 2005/0229719 | A1 | | 10/2005 | Reider et al. |
| 2007/0018659 | A1 | | 1/2007 | Homan et al. |

FOREIGN PATENT DOCUMENTS

| EP | 1306659 | | 2/2003 |
| SU | 427269 | A1 | 5/1974 |
| WO | 0151898 | | 7/2001 |
| WO | 2006104485 | | 10/2006 |

OTHER PUBLICATIONS

International Search report received in corresponding United Kingdom patent application No. GB0822882.7 dated Feb. 3, 2010.
International Search report received in corresponding United Kingdom patent application No. GB0822882.7 dated Mar. 18, 2009.

* cited by examiner

*Primary Examiner* — Hezron E Williams
*Assistant Examiner* — Paul West
(74) *Attorney, Agent, or Firm* — Wong, Cabello, Lutsch, Rutherford & Brucculeri, L.L.P.

(57) ABSTRACT

This invention relates to a measurement tool, and in particular to a measurement tool for use in determining the density and/or viscosity of a stationary or moving fluid. The measurement tool has been designed for use in borehole applications during the location and exploitation of oil and gas reserves. The measurement tool has a resilient pipe with a substantially uniform cross-section along its length, and the fluid is located within the pipe. The pipe carries an exciter which is connected to a signal generator, the exciter and signal generator being adapted to impart transverse and/or rotational oscillations to the pipe. Measuring the frequency of the oscillations can be used to determine the density and/or the viscosity of the fluid within the pipe.

14 Claims, 4 Drawing Sheets

MEASUREMENT TOOL AND METHOD OF USE

CROSS REFERENCE TO RELATED APPLICATION

This application claims priority from Great Britain Application No. 0725199.4, filed Dec. 22, 2007, which is also incorporated herein by reference.

FIELD OF THE INVENTION

This invention relates to a measurement tool, and in particular to a measurement tool for use in determining a parameter of a stationary or moving fluid. The measurement tool has been designed for use in borehole formation testing and the following description will therefore relate primarily to such applications, but the invention is not thereby limited.

BACKGROUND OF THE INVENTION

Measurement tools are in widespread use in borehole formation testing, for example in boreholes drilled into the earth in order to test for or recover underground reserves of oil and/or gas. Some such tools are carried by the drill string and the measurements are carried out during the borehole drilling operation (so-called "measurement-while-drilling" (MWD) or "logging-while-drilling" (LWD) applications). Other measurement tools are used after the borehole has been drilled, the measurement tools being lowered into the borehole by a cable or wire. In highly deviated wells conveyance may be assisted by semi-rigid tubing or by drill-pipe. Still other measurement tools are deployed downhole for lengthy periods of time with or without a connecting cable and are referred to as permanent or retrievable gauges. These are usually for use in production after the exploration phase is complete.

Tools deployed using cable having one or more electrical conductors are generally referred to as "electric wireline tools". The present invention is most likely to be a part of an electric wireline tool, though its use in MWD/LWD or other downhole applications is not thereby excluded.

One known electric wireline tool is a formation testing tool or "pump-out" tool, which is used to extract a volume of fluid from a formation surrounding a borehole, the fluid being tested in order to evaluate the likely productivity of the oil or gas well.

It is a recognised problem of operating formation testing tools that during the borehole drilling operation the fluid within the formation can be contaminated with drilling fluid (or "mud") filtrate typically comprising liquid and other materials. In order to obtain valuable test results it is of prime importance that the formation fluid used for analysis represents virgin formation fluid with little or no contamination from fluids used in the borehole drilling operation.

Drilling fluid is generally divided into oil base mud (OBM) and water base mud (WBM). The drilling fluid pressure is maintained higher than that of the formation, and as a result the drilling fluid seeps into the formation, the seeping fluid being known as filtrate. Fine particles that cannot penetrate the formation are left behind on the borehole wall and build up to form a filter (or "mud") cake. This is relatively impermeable and forms a skin substantially preventing further ingress of fluid. The filtrate displaces virgin formation fluid from the vicinity of the borehole wall, until a stable 'invaded zone' results. Depending on the virgin fluid, the type of mud and the formation composition and structure, different degrees and depth of invasion occur into the formation.

The formation fluid may naturally contain a large percentage of water, of some salinity. Water base mud is predominantly water but need not have the same salinity. Although perfect oil base mud has very little water, in practice it may contain as much as 40% water. Filtrate may include formation water from other depths in the borehole that has mixed into the mud.

DESCRIPTION OF THE PRIOR ART

Traditionally, operators wishing to extract a volume of fluid from a formation surrounding a borehole in order to evaluate the likely productivity of the borehole utilised drill stem testing, in which the formation fluid was pumped to the surface for testing. This practice has become less desirable primarily because of the harmful environmental impact of needing to flare-off excess fluid. Also, there is difficulty in bringing the fluid to the surface from particular boreholes, especially sub-sea boreholes. Furthermore, the pressure and temperature of the fluid changes during its movement to the surface, and these pressure and temperature changes can cause changes in the consistency of the fluid (i.e. the fluid may separate out or otherwise change its material characteristics) which may invalidate the subsequent test.

To overcome the problems associated with pumping the formation fluid directly to the surface, formation testing tools have been developed which can undertake at least some of the tests downhole. One such formation testing tool is described in U.S. Pat. No. 5,602,334, the tool including measurement tools able to measure selected parameters of the formation fluid downhole. This formation testing tool also includes containers which can be filled with formation fluid for transportation to the surface for additional testing if desired.

It is of course necessary that formation testing tools such as that of U.S. Pat. No. 5,602,334 be able to determine whether the fluid being pumped out of the formation is virgin formation fluid, or is contaminated formation fluid, so that the tests are conducted only upon virgin formation fluid, and only virgin formation fluid is collected in the containers. For present purposes "virgin" means having as little contamination as possible, and certainly below some threshold of acceptability.

Many different parameters are desired to be tested downhole, some of which assist in determining whether the fluid is virgin or contaminated, and others which assist the operator in assessing the likely productivity of the formation.

A parameter which can be measured downhole is the electrical resistivity of the fluid. This parameter is often used to determine whether the fluid is virgin or contaminated because the electrical resistivity of oil is significantly different to that of water-base muds. US patent application 2007/0018659 discloses a measurement tool for use in a formation testing tool, the tool measuring the resistivity of the formation fluid.

In US patent application 2007/0018659 the resistivity of the formation fluid is tested as the fluid is flowing along a pipe, and this is a particularly desirable feature of measurement tools used in formation testing tools where the pipe can lie within the formation testing tool. The pipe should preferably be substantially linear and free from constrictions, bends or voids which would induce pressure changes into the fluid, which pressure changes may affect the consistency of the fluid and thereby lead to a different test result than would be obtained upon fluid within the formation.

Another parameter which can be measured downhole is pressure, typically as part of a draw-down and build-up pressure test which can be used to determine the mobility (permeability divided by viscosity) of the fluid in a formation and therefore help to assess the likely productivity of the formation.

Yet another parameter is the chemical constituents of the fluid, which can be used to determine whether the formation fluid at one depth of the borehole is the same as that at another depth, any chemical dis-similarity between the formation fluids at different depths indicating that the formation is not contiguous and is instead made up of discrete reservoirs which will make the oil and/or gas more difficult and expensive to recover. Chemical dissimilarity can also be used to differentiate virgin fluid and filtrate.

The likely productivity of an oil and/or gas reservoir is a very valuable assessment for operators to make as this determines the likely value of the reservoir to the operator. It is an object of this invention to provide a measurement tool which can be used in a formation testing tool and which is able to test more relevant parameters of the formation fluid and/or which is able to test the relevant parameters more accurately and reliably, so that the operator can make a more accurate assessment of the productivity of a particular reservoir.

It is another object of the present invention to assist in distinguishing virgin formation fluid from invasion filtrate ("contamination"), recognising that both the water and oil components in the invaded zone are often a mixture of residual virgin fluid and filtrate, and that virgin fluid beyond the invaded zone may have water or oil similar to that of the mud filtrate.

The measurements of density and viscosity are useful in assessing the contamination of virgin formation fluid by mud filtrate.

Also, the measurement of viscosity is particularly valuable in assessing the productivity of an oil and gas reservoir. As above indicated, a draw-down and build-up pressure test can be used to determine the mobility k of a formation given by $$k = \frac{\mu}{\eta}$$

where $\mu$ is the permeability and $\eta$ is the dynamic viscosity. Thus if the viscosity of the fluid can be determined this will help to determine the permeability of the formation to the fluid within the reservoir, which is more directly related to the likely productivity of the formation.

The dynamic viscosity is related to the kinematic viscosity $v$ and density $\rho$ by the formula $$\eta = \rho v.$$

The measurement of viscosity in the present invention is a function of kinematic viscosity and density so that the density must be measured by some means in order to allow a determination of the dynamic viscosity.

SUMMARY OF THE INVENTION

According to a first aspect of the present invention the measurement tool is adapted to measure the density of a fluid. According to a second aspect of the invention the measurement tool is adapted to measure viscosity of a fluid. According to a third aspect of the invention the measurement tool is adapted to measure both the density and viscosity of a fluid.

According to its first aspect, the present invention provides a measurement tool for measuring the density of fluid within a pipe, the pipe being resilient and having a substantially uniform cross-section along its length, the pipe carrying an exciter, the exciter being connected to a signal generator, the exciter and signal generator being adapted to impart transverse oscillations to the pipe.

It will be understood that a resilient pipe has a resonant frequency of transverse oscillation, the resonant frequency being dependent upon the mass of the pipe. When the pipe is filled with fluid the mass of the fluid affects the resonant frequency and so the resonant frequency can be used to determine the combined mass of the pipe and fluid contained therewithin. Since the mass of the pipe is known, and the volume of the pipe is known, the density of the fluid within the pipe can thereby be determined.

According to its second aspect, the present invention provides a measurement tool for measuring the viscosity of fluid within a pipe, the pipe being resilient and having a substantially uniform cross-section along its length, the pipe carrying an exciter, the exciter being connected to a signal generator, the exciter and signal generator being adapted to impart rotational oscillations to the pipe.

It will be understood that a resilient pipe has a resonant frequency of rotational (or torsional) oscillation, the resonant frequency being dependent upon the torsional resilience of the pipe. When the pipe is filled with fluid the viscosity of the fluid affects the resonant frequency (since a particularly viscous fluid will cause the pipe to behave as if it is substantially solid whereas air or other fluid with very low viscosity will have little effect upon the pipe's resonant frequency of rotational oscillation).

In addition, the pipe will not oscillate only at the resonant frequency, but will also oscillate strongly at frequencies close to the resonant frequency when excited. The amplitude of the response to a forced excitation as a function of excitation frequency near a resonance is a peaked curve. The shape of this curve, centred on the resonant frequency, is commonly termed a "spectrum". The actual shape in practice for resonant pipes is a "Lorentzian" curve. Depending on the particular measurements or calculations made, a spectrum may be presented for example as the ratio of oscillation velocity in response to excitation level (impedance) or their product (power taken from the exciter) at a constant amplitude or constant level of response. In the present invention the spectrum may be derived from any such commonly known means.

Changes in the viscosity of the fluid will not only change the pipe's resonant frequency but will also change the spectrum as viscous friction due to torsional shear affects the power absorbed by the fluid at different frequencies. It is therefore possible to determine viscosity either by observing changes in the resonant frequency, or by observing changes in the shape (primarily the width) of the spectrum, and it is understood that changes in the width of the spectrum are a more accurate method of assessing changes in viscosity, especially at higher viscosities where the spectrum is particularly broad and identification of the peak is difficult.

According to its third aspect, the present invention provides a measurement tool for measuring the density and viscosity of fluid within a pipe, the pipe being resilient and having a substantially uniform cross-section along its length, the pipe carrying an exciter, the exciter being connected to a signal generator, the exciter and signal generator being adapted to impart transverse and rotational oscillations to the pipe.

Preferably, the pipe is "tuned" so that when it is filled with a chosen fluid its resonant frequency of transverse oscillation is substantially different to its resonant frequency of rotational oscillation. The two resonant frequencies can therefore readily be discerned and separated for the measurement of both the density and viscosity of the fluid. Preferably, the pipe is tuned by securing a chosen mass to the outside of the pipe. Desirably, the chosen mass is secured adjacent to the longitudinal centre of the pipe.

Desirably, the same signal generator and exciter are used for both the density and viscosity measurements, the signal generator and exciter being adapted to impart transverse oscillations at a first frequency and rotary oscillations at a second frequency, the second frequency being different to the first frequency.

The exciter can be separate from the detector. For example one embodiment could use a piezoelectric transducer to excite motion and an eddy current proximity sensor pickup coil to measure it.

The signal generator can transmit a range of frequencies to the pipe, the signal generator scanning across the chosen range of frequencies in a chosen period of time. In such embodiments the tool preferably includes a detector which is adapted to determine the response spectrum of the oscillating pipe. The spectrum will allow a determination of the resonant frequency and other desired features.

Alternatively, the signal generator can energise the pipe to oscillate close to or at its resonant frequency, and then the excitation can be stopped and the decaying oscillations observed. The pipe will oscillate at its resonant frequency during this decay, and it is recognised that the decay is exponential with a characteristic decay curve time constant which is inversely related to the spectrum line width that could otherwise be measured. Accordingly, measuring the decay curve can provide information about the spectrum for use in the viscosity (and perhaps also density) measurements.

Alternatively again, the signal generator can be an oscillator whose tuning element is the pipe, in similar known manner as a crystal oscillator has as its resonant element a mechanical resonator (crystal) that forms the tuning element of an electronic circuit. The signal generator thereby excites the pipe at only a single (resonant) frequency. As the resonant frequency changes with changes in the density (and perhaps also the viscosity) of the fluid, the changes can be detected by detecting changes in the output frequency of the signal generator.

In one embodiment the exciter comprises a support secured to the longitudinal centre of the pipe, the support carrying a pair of permanent magnets, and the tool has at least one electrical coil arranged adjacent to each of the permanent magnets, the signal generator being connected to the electrical coils and being adapted to deliver an alternating current to the electrical coils so as to induce a force into the magnets and therefore into the support and pipe. Preferably, the permanent magnets and respective electrical coils are arranged on opposed sides of the pipe. Imparting a similar alternating electrical current into the electrical coils for both magnets causes an alternating force of similar magnitude and direction to be imparted to both of the magnets together, so that the pipe is caused to oscillate transversely. On the other hand, imparting opposing alternating electrical currents into the electrical coils of each magnet causes alternating forces of similar magnitude but opposing direction to be imparted to the magnets so that the pipe is caused to oscillate rotationally.

In other embodiments the two magnets are replaced by a single magnet so that it is not necessary to calibrate the signal generator to accommodate permanent magnets having differing magnetic fields.

The invention also provides a method of use of a measurement tool, the measurement tool having a resilient pipe with a substantially uniform cross-section along its length, the pipe carrying an exciter, the exciter being connected to a signal generator, the method comprising the steps of: {i} issuing an alternating electrical signal from the signal generator to the exciter so as to impart oscillations into the pipe at a first frequency; {ii} measuring the voltage and current flowing to the exciter at the first frequency; {iii} altering the electrical signal from the signal generator so as to impart oscillations into the pipe at a second frequency; {iv} measuring the voltage and current flowing to the exciter at the second frequency; {v} repeating steps {iii} and {iv} at third, fourth etc. frequencies, {vi} determining a response spectrum across the range of frequencies used, and {vii} using the spectrum to determine a characteristic of the oscillations of the pipe.

The characteristic of the oscillations of the pipe may be its resonant frequency, the characteristic corresponding to a chosen parameter of a fluid flowing within the pipe.

The alternation of the electrical signal may be in a number of discrete steps, so that the spectrum comprises a number of measured values at discrete frequencies within the chosen range of frequencies, or it may be continuous (or substantially so).

Alternatively there is provided a method of determining a parameter of a fluid within a pipe, the parameter being one of:
{i} the density of the fluid
{ii} the viscosity of the fluid
{iii} the density and viscosity of the fluid,
the method comprising the steps of:
{a} providing a measurement tool having a resilient pipe with a substantially uniform cross-section along its length, the pipe carrying an exciter, the exciter being connected to a signal generator,
{b} issuing an alternating electrical signal from the signal generator to the exciter so as to impart oscillations into the pipe substantially at its resonant frequency,
{c} stopping the electrical signal to the exciter;
{d} measuring a characteristic of the oscillations after the electrical signal has stopped, and
{e} using the measured characteristic of the oscillations to determine the parameter.

Accordingly, rather than using a "spectrum" method it is possible to use a "decay" method in which oscillations are imparted to the pipe substantially at its resonant frequency (i.e. close enough to the resonant frequency that the pipe will adopt its resonant frequency once the excitation has stopped) and the oscillations are measured after the excitation has stopped.

Preferably, when the parameter is density the measured characteristic is the resonant frequency of transverse oscillations, and when the parameter is viscosity the measured characteristic is the decay curve (and in particular its time constant) of rotational oscillations.

The measurement tool according to all of its aspects has additional benefits in multi-flow formation testing tools such as that described in U.S. patent application Ser. No. 11/626,461 filed on 24 Jan. 2007. In this formation testing tool two (or more) fluid flows from the formation are kept separate and are tested separately, and a measurement tool of the present invention could be arranged in each flow line and direct comparisons between the two fluids could be made as desired. Where one flow line recovers fluid from the formation surrounding the path of the fluid recovered through the other flow line, the comparison can assist in determining when virgin fluid is being recovered and the volume of formation from which recovery is taking place.

BRIEF DESCRIPTION OF THE PREFERRED EMBODIMENTS

The invention will now be described in more detail, by way of example, with reference to the accompanying drawings, in which.

DETAILED DESCRIPTION

Figure 1:
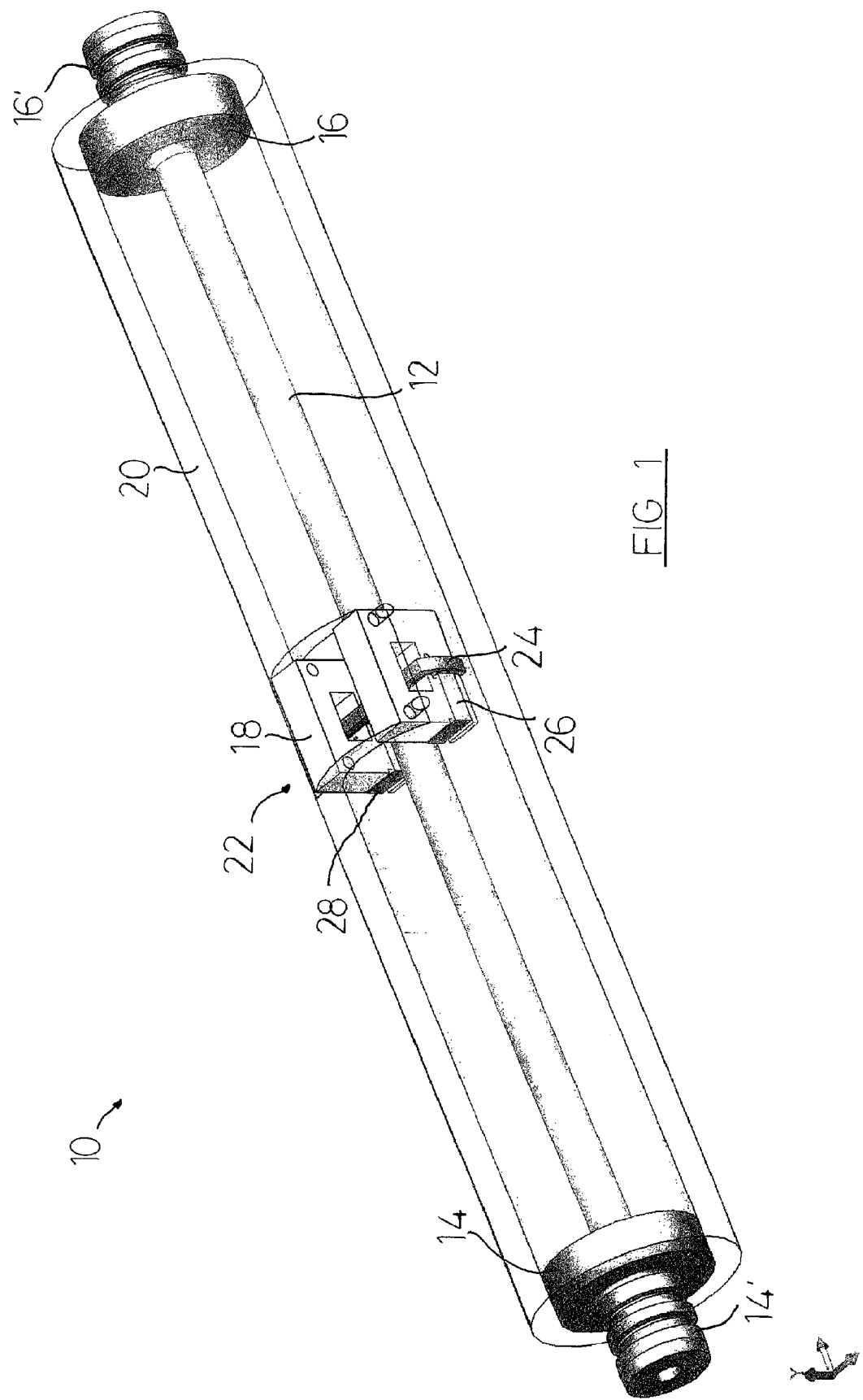
FIG. 1 shows a perspective view of one embodiment of measurement tool according to the invention.

In the drawings, similar numbers are used to represent similar components in the various embodiments.

The measurement tool 10 shown in FIG. 1 comprises a pipe 12, the pipe being resilient and having a uniform cross-section along its length. In this embodiment the pipe has a circular cross-section. The pipe has end connectors 14,16 by which the pipe may be sealingly connected to adjacent pipes, or else to other components within a fluid flow line.

The end connectors are interconnected by a surrounding tube 20 which is substantially rigid, the tube 20 acting to secure the end connectors 14 and 16 in their relative positions, and so secure the respective ends of the pipe 12. In one embodiment the pipe 12 and end connectors 14, 16 are machined from solid and the tube 20 is welded to the end connectors. This results in a minimum number of mechanical joints and therefore reduces the likelihood of a mechanical failure in use. Also, and importantly for the present invention it ensures torsional stress is transmitted from pipe 12 to tube 20 without intermediate elastic compliance or damping due to jointing means. Such compliance or damping would not be easily distinguished in the measurement from that due to the fluid.

By fixing the ends of the pipe 12, the pipe is able to oscillate both transversely (or laterally), and also to oscillate rotationally (or torsionally). The pipe can undergo oscillations according to its fundamental, or first harmonic, frequency (in which the longitudinal centre of the pipe has the maximum amplitude), or according to its second harmonic frequency (in which the longitudinal centre of the pipe remains stationary and the points approximately half way between the longitudinal centre and each of the end connectors undergo the maximum amplitude, or according to its third harmonic frequency, and so on.

End connectors 14 and 16 have respective parts 14' and 16' for sealingly connecting the pipe 12 to the external continuations of the fluid path, so that the volume within pipe 12 is sealed. The fluid within tube 20 is thereby separated from the fluid under measurement and can therefore be controlled, and is desirably air or other gas, in which case the fluid around the pipe 12 has minimal effect upon the transverse and rotational oscillations of the pipe 12.

As the measurement tool 10 is to measure the density of fluid within the pipe it is desirable that the mass of the pipe itself be minimised, so that the tool is more sensitive to the mass of the fluid. As the measurement tool 10 is also to measure the viscosity of fluid within the pipe it is desirable that the pipe be very susceptible to torsional movement, so that the tool readily undergoes torsional oscillations and can be sensitive to the viscosity of the fluid. A titanium pipe having a circular cross-section with an inside diameter of around 6.4 mm (¼ inch) and an outer diameter of around 10 mm (⅜ inch) has been found to be sufficiently lightweight and torsionally resilient for the tool to be sensitive to the mass and viscosity of the fluid within the pipe. In addition, when used in formation testing tools such a pipe is able to withstand the high pressures involved at the typical depths (around 5-10 km) with air or other gas at atmospheric pressure in the volume around the pipe 12.

The pipe 12 carries an exciter 22 which is connected to a signal generator 32 (see FIG. 4), the exciter 22 and signal generator 32 being adapted to impart transverse and rotational oscillations to the pipe 12, as described below.

Similar to the connection between the pipe 12 and tube 20 described above, the construction of the exciter 22 must be such that there is substantially no internal movement or elasticity of its parts, other than the required motion induced across the gap between the stator part fixed to tube 20 and the rotor part fixed to pipe 12. Any unwanted movements or elasticity would result in damping which would not easily be distinguishable in the measurement from that due to the fluid.

In this embodiment the exciter comprises a support 24, electrical coil 26 and electrical coil 28. The support 24 is connected to the longitudinal centre of the pipe 12 (i.e. connected upon the pipe 12 mid-way between the end connectors 14 and 16). As shown in the embodiment of FIG. 3, the support 24 carries two permanent magnets 30, which are preferably substantially identical (i.e. the magnets have as near-identical magnetic fields as possible). The magnets 30 are magnetised (or polarised) perpendicular to the plane of the paper as drawn in FIG. 3, in the same direction, as shown by the solid arrow-heads in FIG. 2. The electrical coil 26 lies adjacent to one of the magnets 30, and the other electrical coil 28 lies adjacent to the other of the magnets 30.

Figure 2:
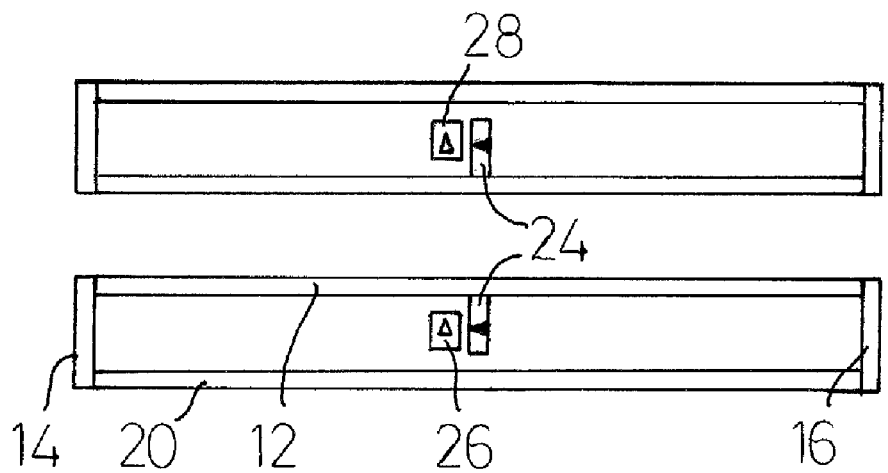
FIG. 2 shows a side view of part of another embodiment of measurement tool according to the invention.
Figure 3:
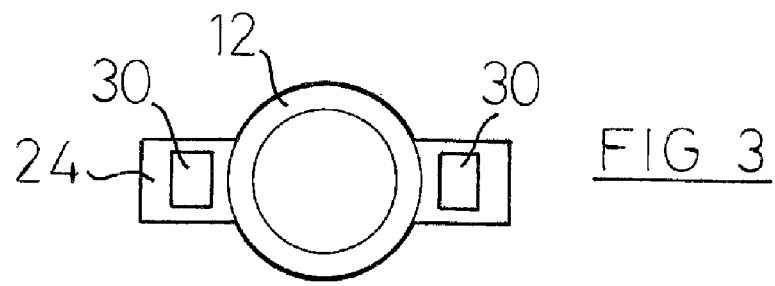
FIG. 3 shows an end view of the yoke and pipe of the measurement tool of FIG. 2.

The flow of electricity around the coils 26 and 28 induces an electric field in the directions shown by the open arrow-heads in FIG. 2, and each of the electric fields imparts a force upon the respective magnet 30 directed out of the paper in the orientation of FIG. 2 (and towards the top of the sheet in the orientation of FIG. 3), for the electric and magnetic fields shown in FIG. 2.

When the magnets 30 are polarised in the same direction, similar (alternating) electric fields of the coils 26 and 28 induce transverse oscillations into the pipe 12, whereas opposed (alternating) electric fields induce rotational oscillations into the pipe 12. If the magnets 30 are polarised in opposing directions this situation is reversed.

Figure 4:
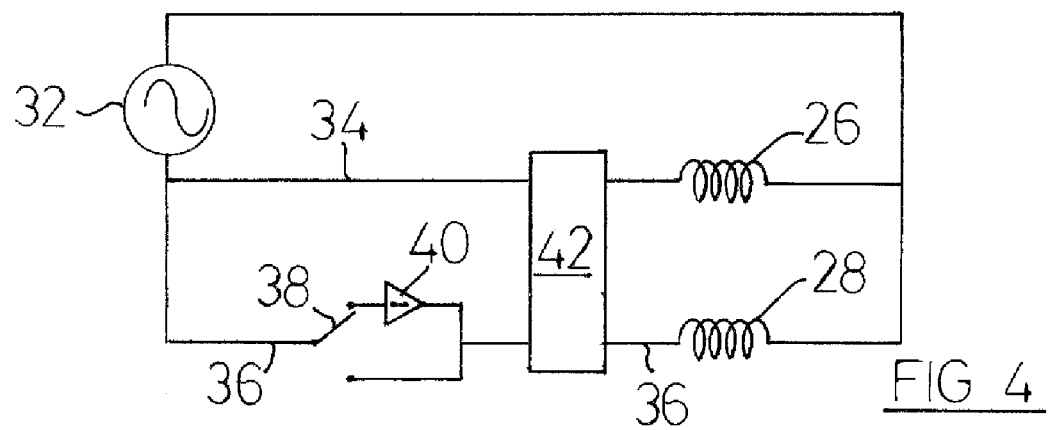
FIG. 4 shows an electrical circuit suitable for exciting oscillations in the pipe.

As shown in FIG. 4, the signal generator 32 is connected to the coil 26 by a first signal wire 34, and to the coil 28 by a second signal wire 36. The second signal wire 36 contains a switch 38 by which an inverter 40 can be switched into or out of the second signal wire, as desired. In this way, the signal generator 32 is able to cause electrical currents of substantially identical magnitude and direction in the respective coils 26 and 28, or currents of substantially identical magnitude but opposed direction in the coils 26 and 28, depending upon the position of the switch 38. (In alternative embodiments in which the magnets 30 are polarised oppositely then the currents must be reversed to achieve the same effect.)

In the embodiment of FIG. 1 the coils 26, 28 are mounted upon respective yokes 18. Preferably the yoke 18 material is of high magnetic permeability and has low eddy current loss as any such loss becomes a part of the absorbed power. Suitable materials for the yokes 18 include laminated steel, bonded iron alloy powder and ferrite, as known for similar applications.

In case the magnets 30 do not have identical magnetic fields across the range of temperatures expected to be encountered, the electrical currents to the coils 26 and 28 will have to differ sufficiently so as to ensure that a substantially identical force is imparted to each of the magnets, so as to ensure that the intended transverse oscillations impart no rotational movement, and vice versa. The forces upon the magnets can be matched either by calibration or empirically.

It will be understood that the pipe 12 will have a resonant frequency of transverse oscillation when empty, and a different resonant frequency when filled with a fluid, the resonant frequency being dependent upon the combined mass of the pipe and the fluid within the pipe 12. Since the mass and volume of the pipe 12 are known the volume of the fluid is known and therefore the mass of fluid within the pipe can be used to determine the density of the fluid.

It will also be understood that the pipe 12 will have a resonant frequency of rotational or torsional oscillation when empty, and a different resonant frequency when filled with a fluid, the resonant frequency being dependent upon the density and viscosity of fluid within the pipe 12. Since the density of the fluid can be determined as above, the viscosity of the fluid can also be determined.

Figure 5:
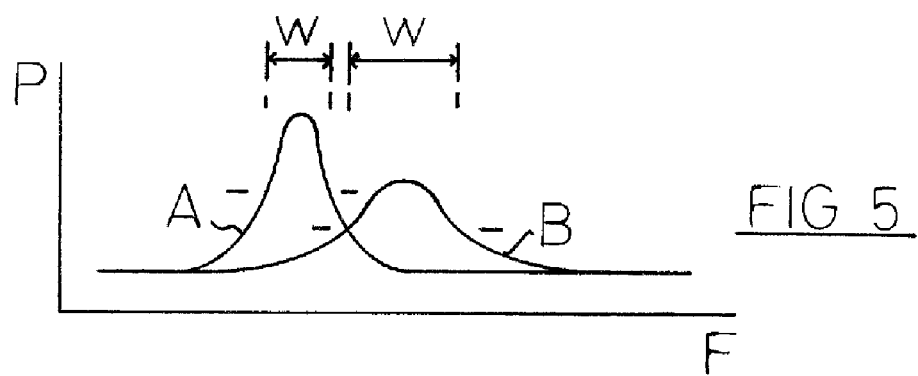
FIG. 5 shows a representation of two spectra for the oscillations in a pipe of a tool such as that of FIG. 1 or FIG. 2.

FIG. 5 shows a schematic representation of two curves showing the power P absorbed by the pipe 12 at a range of frequencies F. The curves A and B represent respective spectra for the rotational oscillations of a pipe 12 filled with two different fluids. The curves A and B show that the resonant frequency (i.e. the peak of the respective curve) differs between the fluids, and also that the shape of the curves differs between the fluids.

To obtain a spectrum such as A or B, it is necessary that the exciter 22 causes the pipe 12 to oscillate with a number of discrete frequencies within a chosen range, or causes the pipe 12 to oscillate across a substantially continuous range of frequencies. In this embodiment the exciter causes the pipe 12 to oscillate at the frequency of the alternating electrical signal issued by the signal generator 32, so that it is necessary for the signal generator 32 to sweep across a chosen range of frequencies, preferably in a chosen period of time. A detector 42 is adapted to measure the voltage and current in each of the signal lines 34 and 36 so as to assess the instantaneous power being imparted to the pipe 12, i.e. the power being imparted at that particular frequency.

It will be understood that the torsional oscillation spectra represented in FIG. 5 comprise a combination of fluid and pipe power losses, the latter being fixed and removable from the calculation by calibration for example.

Considering the viscosity measurement in which the pipe 12 is undergoing rotational oscillations, it is possible to differentiate between the curves A and B by measuring the frequency of the peak of each curve. However, the spectra for torsional oscillations are typically broad, in particular for fluids of high viscosity, so that identifying the actual frequency at which each curve has its peak is technically difficult, and requires an accurate measurement of the actual frequency. Another way to differentiate between the curves A and B is the width of the curve at a chosen value, for example at half the peak value of that particular curve. Accordingly, it will be seen that the width w of the curve B at its half-height is larger than the width w of the curve A at its respective half-height, these curve widths being dependent upon the shape of the spectra, and therefore dependent upon the viscosity of the fluid in the pipe.

Using a measure such as the width of the curve is technically simple as the width of the curve is related to a time measurement by the rate at which the signal generator 32 is sweeping across the range of frequencies. Unlike the peak measurement the curve width does not require absolute measurement of frequency or comparison with the frequency of an empty tube or a tube filled with a reference fluid.

Such curve width measurements are suitable for the rotational oscillations where a peaked spectrum is generated because of power dissipation in the fluid due to its viscosity. However, for transverse oscillations it is preferable to determine the actual resonant frequency because the pipe will only respond strongly very close to the resonant frequency, as the fluid principally moves bodily without internal viscous shear.

Figure 12:
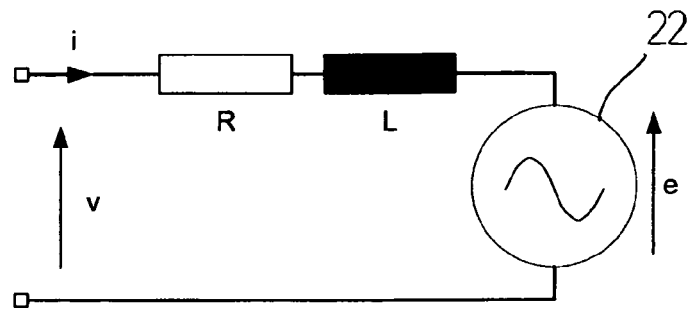
FIG. 12 represents the electrical current, voltage and induced emf of an exciter circuit.

As a general comment, it will be understood that the pipe 12 absorbs power from the exciter 22, but it is not necessary to detect the absorbed power directly. In embodiments in which the exciter is electrically-operated the electro-motive force (emf) e imparted by the exciter 22 (see FIG. 12) is due to transverse and/or rotational movement that results from the input of electrical power, the product of current i and voltage v. The mechanical power is the product of current i and emf e, or ignoring losses in the permeable materials, equivalently the product of torque and angular speed.

If for example the exciter coil is driven at a constant amplitude of current, then the pipe will experience a constant transverse force or rotational torque. As the frequency goes through resonance the motion, and hence emf, will become very large. The input power will go through a peak. This is not always desired.

If, however, the exciter is driven at a constant voltage amplitude then the current will reduce as the frequency goes through resonance. Thus the pipe will experience a transverse or rotational torque, and hence power input, whose magnitude decreases going through resonance. The current therefore represents absorbed power and the spectrum will have a dip rather than a peak. Interpretation of the spectrum measurement depends on the modelling of the source impedance and exciter winding impedance, as the applied voltage is reduced by the current flowing through these impedances.

Accordingly, reference herein to 'power spectrum' should be interpreted more generally as a response spectrum, as the actual spectrum being detected could be the electrical current for example, and be a peak or a dip.

It is understood that density can be determined from the frequency measurement, and the spectrum is not required. Conversely, it is understood that the viscosity measurement typically requires the response spectrum if the pipe is continuously excited, or the decay curve if applicable. In such applications, the use of frequency and spectrum together can be used in corroborating a measurement.

It will also be understood that in measurements requiring the identification of the peak of the spectrum it is possible to make the resonant pipe with the exciter as the tuned component of an electrical oscillator. In such embodiments the oscillator frequency always drives itself to the peak of the pipe response, i.e. to the resonant frequency, and changes in the fluid density will be detectable by changes in the output of the signal generator.

Figure 6:
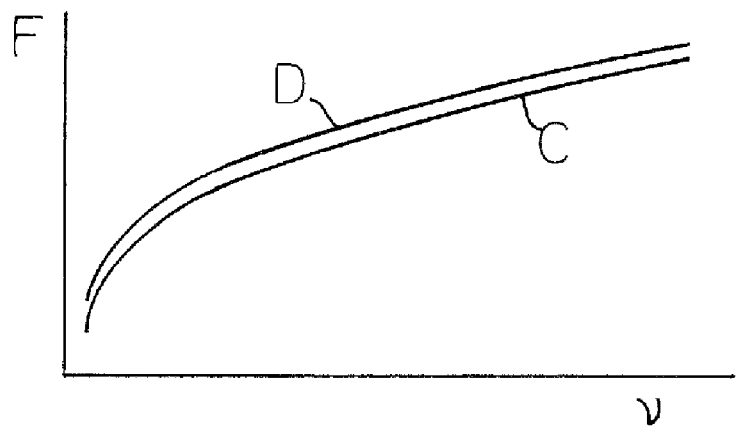
FIG. 6 shows two curves representing measurements upon the spectra of FIG. 5.

FIG. 6 shows two curves, the first curve C representing the resonant frequency versus fluid kinematic viscosity v (i.e. the frequency of peak power being imparted to the pipe 12), the second curve D representing the width w of the spectrum at half of the peak power value, again versus kinematic viscosity v. These curves represent calculations undertaken by one of the inventors, and demonstrate that the shape of the curves is substantially identical, and therefore that both of these determinations is equally valid in determining the viscosity of the fluid. (As indicated above the spectra for rotational oscillations are also dependent upon the density of the fluid, and fluids of differing density have different curves to those of C or D, but once the density is known a measure of the peak frequency, curve width or decay curve can give a measure of viscosity).

It is desirable to utilise the fundamental frequency of oscillation of the pipe 12 and to avoid the second and other harmonics. (The pipe 12 will not easily be excited into its even harmonics by excitation at the centre of the pipe 12 as that is a nodal point for these harmonics.) An appropriate range of frequencies to be issued by the signal generator 32 can be chosen by calculation or experiment depending upon the range of fluids likely to be encountered by the tool in practice.

In embodiments in which the same pipe 12 is used to measure both of the density and viscosity, it will be understood that the exciter 22 can be used to impart both transverse and rotational oscillations into the pipe 12. The pipe 12 will be able to undergo both of these oscillations together so that the density and viscosity can be determined together, on the same volume of fluid. Clearly, in such embodiments it is necessary that the frequency range used for the transverse oscillations does not interfere with (and preferably not overlap with) the frequency range used for the rotational oscillations. A chosen mass can be added (preferably to the centre of the pipe 12) to "tune" the pipe so that the fundamental frequencies of the transverse and rotational oscillations are kept apart. This mass can conveniently be an integral part of the exciter construction.

Figure 7:
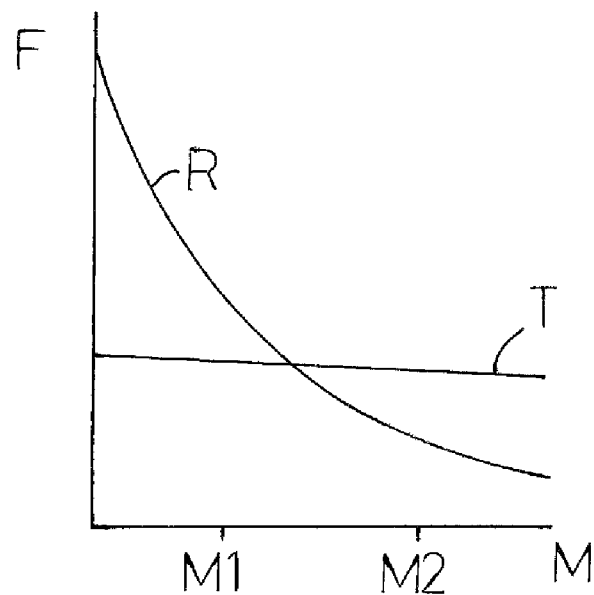
FIG. 7 shows two curves representing the effect of adding a mass upon the resonant frequencies of the oscillation of a pipe.

FIG. 7 shows a representation of the effect of adding a disc of mass M to the outside of the pipe 12 at its longitudinal centre, upon the resonant frequency F for both transverse oscillation T and rotational oscillation R. Again, these curves represent calculations undertaken by one of the inventors.

It will be observed that the addition of a relatively small mass M (up to around 20 grammes) has little effect upon the (fundamental) resonant frequency of transverse oscillation T, but a much greater effect upon the (fundamental) resonant frequency of rotational oscillation R. Using calculations or experiment to determine actual frequency curves for a given pipe 12 would enable the choice of a suitable mass M to values such as M1 or M2, where the resonant frequencies for the different oscillations are well apart. (In practice also, care would have to be taken to avoid the possible harmonic frequencies).

In an embodiment using a titanium tube as above described, of length 30 cm, the fundamental resonant frequency for transverse oscillation T is around 500 Hz. With mass M1 of around 5 grammes the fundamental resonant frequency for torsional oscillation is around 4,000 Hz. These frequencies are far enough apart so that their spectra do not overlap. It would be possible to use a lesser mass M, but at higher frequencies the excitation of the fluid within the pipe 12 is reduced (and above around 5,000 Hz there is little excitation of the fluid under rotational oscillation) and therefore determinations of viscosity are less reliable.

It will be understood that the radial distribution of the mass M relative to the pipe 12 is also relevant, as a mass located close to the pipe 12 will have a lesser effect upon the resonant frequency of rotational oscillation than the same mass spaced away from the pipe, the rotational resonant frequency being affected by the mass moment of inertia about the pipe axis and the transverse resonant frequency by the mass alone.

The tool 10 in these embodiments has only a single signal generator 32 and a single set of coils 26, 28 to generate the transverse oscillations at a first frequency range and the rotational oscillations at a second frequency range. This can be achieved by switching the switch 38 to its non-inverting position for a first period of time and driving the pipe 12 to oscillate transversely at a chosen frequency (or a chosen number or range of frequencies), then switching the switch 38 to its inverting position and driving the pipe 12 to oscillate rotationally at a chosen frequency (or a chosen number or range of frequencies). This cycle is repeated across the full range of frequencies chosen, and then the whole cycle is repeated so that the density and viscosity of the fluid can be determined on a substantially continuous basis.

The frequency at which the switch 38 is moved between its inverting and non-inverting positions can be chosen as desired. If the signal generator 32 generates a number of discrete frequencies then changes between the different frequencies can be coordinated with movements of the switch 38. Desirably with one signal generator the frequency sweeps for viscosity and for density will be alternated.

In alternative embodiments there are two signal generators in series, or two signal generators with a set of coils for each (a second set of coils could be located to the right of the support 24 in FIG. 2, for example), one of the signal generators causing the pipe to oscillate transversely at a first frequency and the other of the signal generators causing the pipe to oscillate rotationally at a second frequency. The signal generators may be implemented in digital or analogue circuitry, in the former case using a digital to analogue converter to output the signal. Simultaneous measurement is possible because of the distinct frequencies of transverse and torsional oscillation.

If will be appreciated that the exciter disclosed herein is only one of a large number of configurations of magnets and coils that can be used to impart motion to the pipe.

Figure 8:
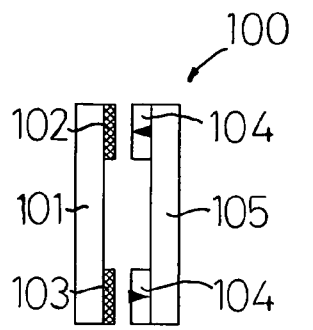
FIG. 8 shows a magnet and coil arrangement for an alternative exciter.
Figure 9:
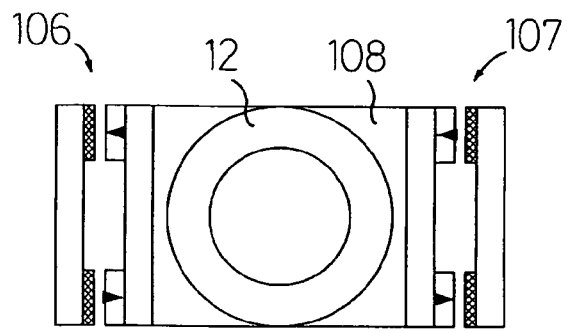
FIG. 9 shows an exciter using two of the magnet and coil arrangements of FIG. 8.

FIG. 9 discloses an exciter 122 where two exciters 106 and 107 are disposed on opposite sides of the pipe 12 and affixed thereto by flange 108. An exciter 100 is shown in FIG. 8 and comprises a magnetically permeable stator 101 with low eddy current loss carrying coil sides 102 and 103, and a magnetically permeable rotor 105 carrying magnets 104 polarised as shown by the solid arrow-heads. Conveniently the coil sides 102, 103 are part of one coil arranged so that current flowing into the paper on side 102 returns out of the paper on side 103. Applying current to the coil in the presence of the permanent magnetic field will cause the rotor and stator to move relatively. In the exciters 106 and 107 (each of which has the same form as the exciter 100) the rotor is shown fixed to the pipe 12 and the stators are fixed to the tube (such as tube 20), but the roles of stator and rotor are interchangeable. By applying the signal in the same or opposite polarities to the two exciters transverse (up and down in the plane of the page) and torsional oscillations may be imposed.

The above-described permanent magnet embodiments use the exciter coils for both exciting motion and measuring it. One skilled in the art could however devise a separate coil system just for obtaining the required measurements.

Whilst in some applications it is preferred to use balanced exciters 106 and 107, in tests using the decay and spectrum methods it has been found that the pipe 12 can be excited into transverse and rotational oscillations by the excitation of only one of the exciters 106 or 107. Thus, provided that the resonant frequencies of the transverse and rotational oscillations are sufficiently far apart then exciting the pipe with the exciter 106 or 107 substantially at the resonant frequency for transverse oscillations and then stopping the excitation results in the pipe undergoing transverse oscillations at the resonant frequency for those oscillations. There is no tendency to impart rotational oscillations despite the apparent use of an unbalanced exciter. Similarly, rotational oscillations can be imparted by an exciter 106 or 107 exciting the pipe 12 substantially at the resonant frequency for those oscillations.

In arrangements such as that shown in FIG. 9, one of the exciters 106, 107 can be used to impart oscillations into the pipe whilst the other exciter 107, 106 can be used to detect the oscillations. In an alternative arrangement the same component 106, 107 can be used both an exciter and as a detector.

Figure 10:
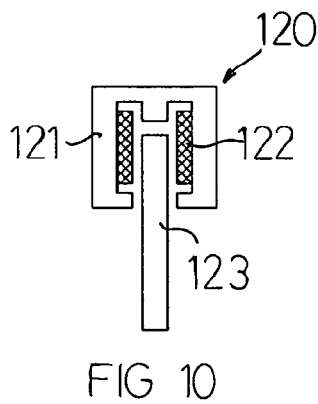
FIG. 10 shows a solenoid arrangement for another alternative exciter.
Figure 11:
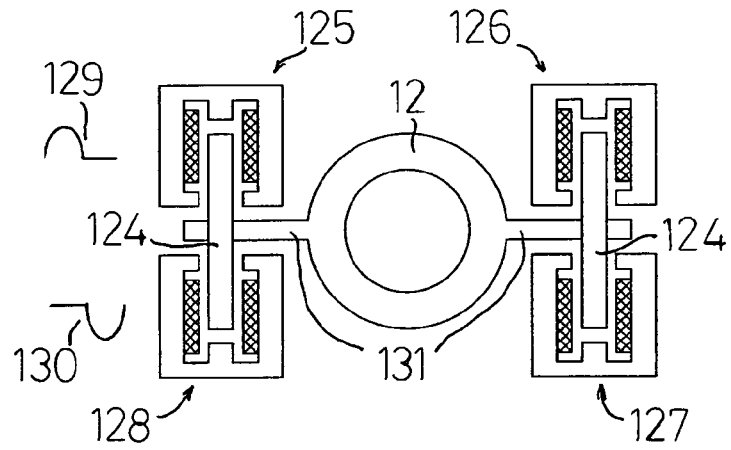
FIG. 11 shows an exciter using four of the solenoid arrangements of FIG. 10.

An alternative embodiment which does not require the use of magnets is shown in FIGS. 10 and 11. A rudimentary solenoid 120 comprises an iron stator 121, an iron plunger 123 and a solenoidal coil 122, where iron is just one example of suitable magnetically permeable materials. The application of a current of any polarity to the coil will draw the plunger 123 into the stator 121. A solenoid is just one example of a variable reluctance motor in which coil inductance changes with rotor or plunger position.

Four such rudimentary solenoids 125, 126, 127 and 128 affixed to a tube (not shown) may be disposed about the pipe 12 at its mid section. Plungers 124 are fixed to the pipe 12 by brackets 131. The signal generator(s) output current may be divided into a positive half cycle (represented at 129) and a negative half cycle (represented at 130), by well-known circuit techniques. If the positive half cycle is applied to solenoids 125 and 126 then the pipe will be drawn upwards. If the negative half cycle is applied to solenoids 127 and 128 then the pipe will be drawn downwards. Thus continuous transverse oscillation is imposed on the pipe. Conversely if the positive half cycle is applied to solenoids 125 and 127 and the negative half cycle to solenoids 126 and 128, continuous torsional oscillation is imposed. If a signal current of a frequency which is sufficiently high or sufficiently different from the resonant frequencies such that it has no measurable effect on pipe movement is applied to the solenoids then the voltage measured at this frequency across the unenergised coils is a measure of their inductance and hence pipe movement. This is an alternative means of measurement.

It will be appreciated that the imposed vibrations are of minute amplitude and practically any embodied exciter may be considered to impart linear local motion even for torsion, so that for example the solenoidal embodiment may be constructed with parallel solenoids as shown.

It will be understood that the determinations of density and viscosity are substantially independent of whether the fluid is stationary or flowing, and the invention in all aspects is therefore suitable for use in a formation testing tool where fluid is being pumped along the pipe 12 within the testing tool. Accuracy will depend on the relative times to make the measurements and the transit time of fluid of varying properties through the pipe. The invention reduces measurement time by allowing both measurements to be taken simultaneously or substantially so, and it ensures coherent measurements by making them on the same body of fluid in the same physical conditions.

The tool 10 can be calibrated with fluids having known densities and viscosities, in which case the tool can be used quantitatively. Alternatively, the tool 10 can be used qualitatively, so as to determine changes in density or viscosity of a fluid flowing through the pipe 12, or to compare the density and/or viscosity of fluids flowing in separate pipes 12.

It will also be understood that all of the disclosed embodiments may be used in methods employing the continuous excitation of the pipe across a range of frequencies (the "swept or stepped method"), in methods employing the excitation of the pipe followed by the decay of the oscillations (the "decay method"), and in methods in which the signal generator and exciter are tuned to the pipe's resonant frequency.

In the third of these alternative methods the signal generator and exciter act as the mechanical resonator part of an electromechanical oscillator. The frequency of the oscillator is automatically at the peak of the spectrum. The mechanical resonator provides an impedance for torsion that is a function of its inertia and torsional elasticity, and for transverse motion that is a function of density and elasticity. The elements are respectively analogous to capacitance C and inductance L, with spectrum width or decay time analogous to a resistive element R. It is well known to those skilled in the art how to make such RLC elements into an oscillator using an electronic amplifier. A crystal oscillator is a common example, where the crystal's electromechanical resonance is exploited in regenerative feedback of an electronic amplifier. In the present invention the exciter and measurement circuit becomes an interface between the electronics and the resonator.

As concerns the first and second of these alternative methods, the signal generator and related electronics can permit both methods. The relative advantages and disadvantages of each of these methods are summarised as follows:

|  | Swept or stepped method | Decay method |
| --- | --- | --- |
| Time | The frequency sweep has to be slow enough for the pipe and fluid inertia to follow it. For example if the sweep is stepped then one needs to be sure the excitation at one frequency has stabilised to allow the measurement to be made before exciting the next. This can take quite a long time (eg compared to the transit time of fluid in the pipe). | A tone burst at the anticipated frequency, preferably with a smooth amplitude envelope, has enough energy and bandwidth to excite the pipe quickly whilst not exciting other modes. |
| Detection | An electrical exciter has an internal impedance due to the coils' inductance and resistance. This impedance is in series with the emf e induced in the coil by | Once the tone burst is completed the pipe excitation decays slowly. There is no excitation current and the internal impedance of the exciter has no effect on the measurement - voltage v is the same |

| Swept or stepped method | Decay method |
|---|---|
| pipe motion. When the exciter is being driven, the excitation current causes a voltage drop across the internal impedance. This voltage drop, in series with the emf, means that the measurable exciter voltage v is not entirely due to motion - the impedance has to be compensated for by computation or possibly by making a bridge circuit. A phase-sensitive detector to maximise the measurement signal-noise ratio can be used as the motion is synchronous to the excitation current. For simultaneous measurement of density and viscosity the spectra must be separated by filtering before separate phase-sensitive detectors may be used. | as motional emf e. Measurement of the decaying signal to measure the frequency and/or decay rate (energy loss) cannot use a phase-sensitive detector as there is no reference signal. For simultaneous measurement of viscosity and density the superimposed decay curves must be separated by filtering or a parameter estimation method used to extract the different characteristics. For example a single decay curve may be characterised in the present invention by four unknown parameters of amplitude, decay time constant, frequency and phase. This becomes eight parameters with superimposed curves. By way of example a recording of 1000 samples at 50 kHz sampling rate will be found to give good estimates using the known Levenberg-Marquardt algorithm. Of the eight parameters the decay time constant is most useful for viscosity and frequency is most useful for density, as already explained. |

Use of an exciter and separate motion detector combines the advantages of the above but is more complicated to implement.

It is presently preferred to measure the density of the fluid by exciting the pipe substantially at its resonant (transverse) frequency and then stopping the excitation. The pipe oscillations will decay at the resonant frequency and the resonant frequency can be measured and used to determine the density of the fluid. Also, it is presently preferred to measure the viscosity of the fluid by exciting the pipe substantially at its resonant (rotational) frequency and then stopping the excitation. The pipe oscillations will decay and the decay curve, and in particular its time constant, can be measured and used to determine the viscosity of the fluid. The measurements can be rapidly interleaved or made at the same time and the superimposed decay curves analysed as previously described.

The invention claimed is:

1. A measurement tool comprising a pipe;
   the pipe being resilient and having a substantially uniform cross-section along its length;
   an exciter carried by the pipe and being located at the longitudinal centre of the pipe;
   a signal generator connected to the exciter, the signal generator and exciter being adapted to impart transverse and rotational oscillations to the pipe;
   a detector located at the longitudinal centre of the pipe, the detector being adapted to detect the transverse oscillations and the rotational oscillations of the pipe; and
   means to measure the resonant frequency of the transverse oscillations of the pipe and to determine the density of a fluid within the pipe from the resonant frequency of the transverse oscillations, and to measure the decay curve of rotational oscillations of the pipe and to determine the viscosity of the fluid within the pipe from the decay curve of the rotational oscillations.

2. A measurement tool according to claim 1 in which the signal generator is adapted to transmit a predetermined range of frequencies to the pipe over a predetermined period of time.

3. A measurement tool according to claim 1 in which the signal generator is adapted to energise the pipe to oscillate substantially at its resonant frequency for transverse oscillations, and substantially at its resonant frequency for rotational oscillations.

4. A measurement tool according to claim 1 in which the pipe has a resonant frequency of transverse oscillations and a resonant frequency of rotational oscillations, the resonant frequency of transverse oscillations being substantially different to the resonant frequency of rotational oscillations.

5. A measurement tool according to claim 4 having a tuning mass secured adjacent to the longitudinal centre of the pipe.

6. A measurement tool according to claim 1 having a single signal generator and a single exciter, adapted to impart transverse oscillations at a first frequency and rotational oscillations at a second frequency, the second frequency being different to the first frequency.

7. A measurement tool according to claim 1 in which a single component provides the exciter and the detector.

8. A measurement tool according to claim 1 in which said fluid is a first fluid within a first pipe, said exciter is a first exciter, said signal generator is a first signal generator, and in which the tool further comprises a second pipe, the second pipe being resilient and having a substantially uniform cross-section along its length;
   a second exciter carried by the second pipe and being located at the longitudinal centre of the second pipe;
   a second signal generator connected to the second exciter, the second signal generator and second exciter being adapted to impart transverse and rotational oscillations to the second pipe;
   a second detector located at the longitudinal centre of the second pipe, the second detector being adapted to detect the transverse oscillations of the second pipe and the rotational oscillations of the second pipe; and
   means to measure the resonant frequency of the transverse oscillations of the second pipe and to determine the density of a fluid within the second pipe from the resonant frequency of the transverse oscillations, and to measure the decay curve of rotational oscillations of the second pipe and to determine the viscosity of the fluid within the second pipe from the decay curve of the rotational oscillations.

9. A measurement tool according to claim 8 in which the transverse and rotational oscillations are imparted to the first pipe, and the transverse and rotational oscillations are imparted to the second pipe, substantially simultaneously.

10. The method according to claim 8 in which the group of steps {ii}-{v} and the group of steps {vi}-{ix} are undertaken repeatedly and simultaneously.

11. The method according to claim 8 in which the group of steps {ii}-{v} and the group of steps {vi}-{ix} are undertaken repeatedly and alternately.

12. A measurement tool according to claim 1 in which the exciter comprises a support secured to the longitudinal centre of the pipe, the support carrying at least one permanent magnet, the tool having at least one electrical coil arranged adjacent to the permanent magnet, the signal generator being connected to the electrical coil and being adapted to deliver an alternating current to the electrical coil so as to induce an oscillating force into the magnet and therefore into the support and pipe.

13. A method of determining the density and the viscosity of a fluid within a pipe, the method comprising the steps of:
{i} providing a measurement tool having a resilient pipe with a substantially uniform cross-section along its length, the pipe carrying an exciter at the longitudinal centre of the pipe, the exciter being connected to a signal generator, the tool also having a detector located at the longitudinal centre of the pipe;
{ii} issuing a first alternating electrical signal from the signal generator to the exciter so as to impart transverse oscillations into the pipe substantially at its resonant frequency for transverse oscillations;
{iii} stopping the first electrical signal to the exciter;
{iv} measuring the frequency of the transverse oscillations,
{v} using the frequency of the transverse oscillations to determine the density of the fluid,
{vi} issuing a second alternating electrical signal from the signal generator to the exciter so as to impart rotational oscillations into the pipe substantially at its resonant frequency for rotational oscillations;
{vii} stopping the second electrical signal to the exciter;
{viii} measuring the decay curve of the rotational oscillations, and
{ix} using the decay curve of the oscillations to determine the viscosity of the fluid.

14. A measurement tool comprising a pipe;
the pipe being resilient and having a substantially uniform cross-section along its length;
an exciter carried by the pipe and being located at the longitudinal centre of the pipe;
a signal generator connected to the exciter, the signal generator and exciter being adapted to impart transverse and rotational oscillations to the pipe;
a detector located at the longitudinal centre of the pipe, the detector being adapted to detect the transverse oscillations and the rotational oscillations of the pipe; and
means to measure the resonant frequency of the transverse oscillations of the pipe and to determine the density of a fluid within the pipe from the resonant frequency of the transverse oscillations, and to measure the decay curve of rotational oscillations of the pipe and to determine the viscosity of the fluid within the pipe from the decay curve of the rotational oscillations,
the means to measure the resonant frequency of the transverse oscillations of the pipe being adapted to measure the resonant frequency whilst the signal generator and exciter are not imparting transverse oscillations to the pipe.

* * * * *

UNITED STATES PATENT AND TRADEMARK OFFICE
CERTIFICATE OF CORRECTION

| | | |
|---|---|---|
| PATENT NO. | : 8,281,646 B2 | Page 1 of 1 |
| APPLICATION NO. | : 12/335981 | |
| DATED | : October 9, 2012 | |
| INVENTOR(S) | : Waid et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 737 days.

Signed and Sealed this
Twelfth Day of August, 2014

Michelle K. Lee
*Deputy Director of the United States Patent and Trademark Office*